Jan. 15, 1974 B. J. MACHIN Plant Pat. 3,435
CHRYSANTHEMUM PLANT
Filed Dec. 27, 1971
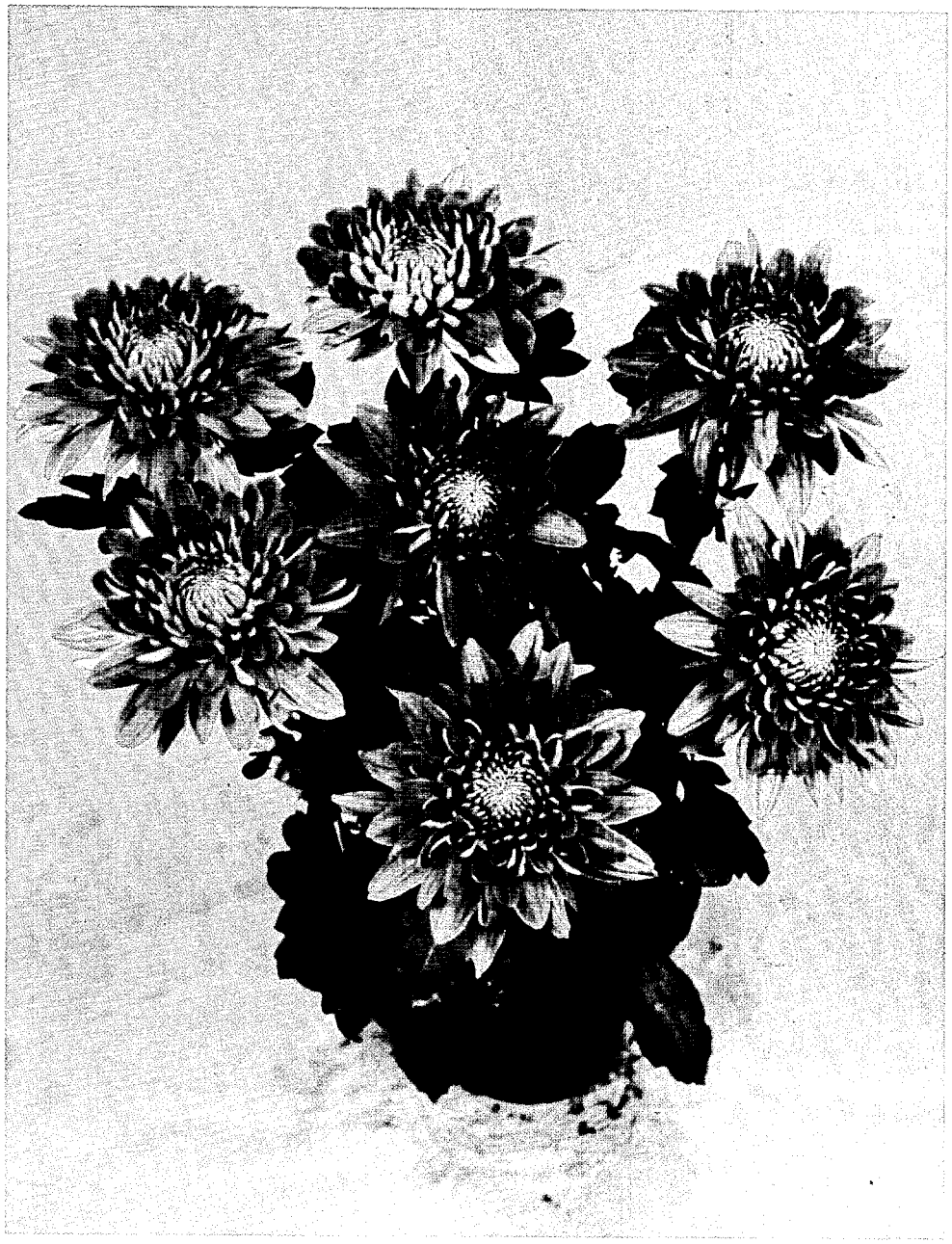

United States Patent Office

Plant Pat. 3,435
Patented Jan. 15, 1974

3,435
CHRYSANTHEMUM PLANT

Barrie John Machin, East Broyle Estate, England, assignor to Frampton's Nurseries Limited, Chichester, Sussex, England Filed Dec. 27, 1971, Ser. No. 212,830
Int. Cl. A01h 5/00
U.S. Cl. Plt.—81 1 Claim This invention relates to a new and distinct variety of *Chrysanthemum morifolium* Bailey, pot type, known as Magnum.

Magnum is a seedling originated by me from a cross made in 1966 between the unpatented variety Redcap and the unpatented variety Frolic, the former being the seed parent, and the latter being the pollen parent.

The variety Magnum resulted from an extensive breeding program with the object of producing improved varieties for year round pot chrysanthemum with more uniformity and better response under poor light conditions as compared with existing varieties.

Magnum has the following improved characteristics over the Princess Anne range of varieties.

(1) Due to its shorter internode length, the height of the plant can be controlled more easily, using daylength or chemical dwarfing control measures.
(2) Although the flowers are smaller, their incurving form is much improved and more flowers per plant are obtained.
(3) The intense color is not available in the Princess Anne range of varieties.
(4) Response is much more uniform under poor winter light conditions.

As compared with its seed parent, Magnum is mauve rather than red, has larger, more luxuriant foliage, produces more shoots after pinching, which flower in a more uniform manner and makes a better pot plant.

As compared with its pollen parent, Magnum has a larger flower size and a deeper color.

Asexual reproduction of this new variety Magnum by rooting vegetative shoots in Sussex, England, shows that the above characteristics are fixed and come true to type through succeeding generations.

The accompanying drawing shows a typical flower of my new variety depicted in color as nearly true as it is reasonably possible to make the same in a color illustration of this character.

The following is a detailed description of the new variety Magnum with color terminology in accordance with the Royal Horticultural Society Color Chart, hereinafter referred to as RHS.

Genus—Chrysanthemum
Species—*Morifolium* Bailey
Type—Pot
Class—Incurving decorative Breeding: The original seedling resulted from a cross between the varieties Redcap and Frolic, the former being the seed parent, the latter being the pollen parent. The cross was made in 1966 at Frampton's Nurseries Ltd., Forbridge Nursery, Chichester, Sussex, England.

Propagation: Holds its distinguishing characteristics through succeeding propagations by rooting vegetative shoots.

Flower: When grown and observed in Sussex, England, in 3½ inch pots and pinched, up to 6 flowers per plant are formed. When five plants are planted per 5 inch pot, 4 to 5 flowers are borne on each plant.

Bloom:
*Size.*—Average diameter is 8 to 9 cm. when fully open.
*Petalage.*—Incurving decorative with approximately 170 to 200 ray petals and five disc petals.
*Form.*—Incurving decorative.
*Petals.*—Long, broad, overlapping, blunt, flat and of medium texture.

Color of open bloom:
Inner face of fully expanded petal, RHS 67A.
Outer face of fully expanded petal, RHS 74C.
Inner face of young petal, RHS 61A.
Outer face of young petal, RHS 74C.

Response Group: 10 weeks.
Temperature tolerance: 55–60° F. at night.
Plant: Stocky well branched habit of growth.

Foliage:
Good quality; average internode length 1½ to 2 cm.
Medium size.
Color, RHS 137B; medium texture.

Stem:
Thick and strong.
Color, RHS 145C at flowering.

I claim:

1. A new and distinct variety of *Chrysanthemum morifolium* Bailey, pot type, substantially as herein shown and described characterized particularly as to novelty by its unique combination of an intense purple color, luxuriant foliage, an increased number of flowers per plant, and uniform response under poor winter light conditions.

No references cited.

ROBERT E. BAGWILL, Primary Examiner